(12) United States Patent
Peng et al.

(10) Patent No.: US 9,291,560 B2
(45) Date of Patent: Mar. 22, 2016

(54) CHARACTERIZATION OF NEAR FIELD TRANSDUCERS

(71) Applicant: Seagate Technology LLC, Cupertino, CA (US)

(72) Inventors: Chubing Peng, Eden Prairie, MN (US); Lifu Zhou, Eden Prairie, MN (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 131 days.

(21) Appl. No.: 13/794,706

(22) Filed: Mar. 11, 2013

(65) Prior Publication Data

US 2013/0277575 A1 Oct. 24, 2013

Related U.S. Application Data

(60) Provisional application No. 61/637,507, filed on Apr. 24, 2012.

(51) Int. Cl.
*G01N 21/64* (2006.01)
*G11B 5/60* (2006.01)

(52) U.S. Cl.
CPC ............ *G01N 21/64* (2013.01); *G01N 21/6489* (2013.01); *G11B 5/6088* (2013.01)

(58) Field of Classification Search
CPC .......................... G01N 21/64; G01N 21/6489
USPC ........................................... 250/458.1, 459.1
See application file for complete search history.

(56) References Cited

U.S. PATENT DOCUMENTS

| | | |
|---|---|---|
| 4,855,792 A | 8/1989 | Holbrook et al. |
| 6,429,968 B1 | 8/2002 | Carver |
| 8,149,653 B2 | 4/2012 | Shimazawa et al. |
| 8,243,561 B2 | 8/2012 | Matsumoto |
| 8,369,191 B2 | 2/2013 | Shimazawa |
| 8,391,107 B2 | 3/2013 | Gage et al. |
| 8,395,971 B2 | 3/2013 | Sasaki et al. |
| 8,406,089 B2 | 3/2013 | Sasaki et al. |
| 8,406,090 B2 | 3/2013 | Juang et al. |
| 8,432,781 B2 | 4/2013 | Knappmann et al. |
| 2007/0177149 A1* | 8/2007 | Aronkyto et al. ............. 356/417 |
| 2008/0055784 A1 | 3/2008 | Shimazawa et al. |
| 2009/0225464 A1 | 9/2009 | Juang et al. |
| 2010/0246907 A1 | 9/2010 | Wachman et al. |
| 2011/0055984 A1 | 3/2011 | Cheng et al. |
| 2011/0122402 A1* | 5/2011 | Westphal ...................... 356/217 |
| 2011/0216635 A1 | 9/2011 | Matsumoto |

(Continued)

OTHER PUBLICATIONS

Peng, "Surface-plasmon resonance of a planar lollipop near-field transducer", Applied Physics Letters, vol. 94 (171106), 2009, pp. 1-3.

(Continued)

*Primary Examiner* — Mark R Gaworecki
(74) *Attorney, Agent, or Firm* — Hollingsworth Davis, LLC

(57) ABSTRACT

An approach for characterizing an optical near field transducer (NFT) involves providing excitation radiation to the NFT. The NFT emits photoluminescent radiation in response to the excitation radiation. The output radiation from the NFT is filtered so that a portion of the photoluminescent radiation emitted by the NFT passes through the filter and the excitation radiation is substantially blocked. A detector detects the portion of photoluminescent radiation and outputs an electrical signal in response to detection of the portion of photoluminescent radiation.

19 Claims, 14 Drawing Sheets

(56) References Cited

U.S. PATENT DOCUMENTS

| | | |
|---|---|---|
| 2011/0228651 A1 | 9/2011 | Gage et al. |
| 2011/0228652 A1 | 9/2011 | Gage et al. |
| 2011/0228653 A1 | 9/2011 | Shimazawa et al. |
| 2011/0299080 A1 | 12/2011 | Peng |
| 2012/0090162 A1 | 4/2012 | Shimazawa et al. |
| 2012/0092971 A1 | 4/2012 | Schreck et al. |
| 2012/0120387 A1* | 5/2012 | Meloni et al. ............ 356/72 |
| 2012/0134246 A1 | 5/2012 | Shimazawa |
| 2012/0163137 A1 | 6/2012 | Wang et al. |
| 2012/0257488 A1 | 10/2012 | Knappmann et al. |
| 2013/0126755 A1 | 5/2013 | Kemnitz |
| 2013/0135975 A1 | 5/2013 | Gage et al. |
| 2014/0050486 A1 | 2/2014 | Bain et al. |
| 2015/0036470 A1 | 2/2015 | Balamane et al. |

OTHER PUBLICATIONS

Muhlschlegel et al., "Resonant Optical Antennas", Science, vol. 308 (5728), Jun. 2005, pp. 1607-1609.

U.S. Appl. No. 13/931,019, filed Jun. 28, 2013, Peng.

Czichis et al., "Micro Spectroscopy" "Springer Handbook of Materials Measurement Methods", 2006, pp. 549-550.

Hall, "The Design and Implementation of a Photoluminescence Experiment", Sep. 24, 1999, 10 pages.

International Search Report and Written Opinion dated Aug. 14, 2013 from PCT Application No. PCT/US2013/038005, 10 pages.

U.S. Appl. No. 13/959,440.

\* cited by examiner

CHARACTERIZATION OF NEAR FIELD TRANSDUCERS

RELATED PATENT DOCUMENTS

This application claims the benefit of provisional Patent Application Ser. No. 61/637,507 filed on Apr. 24, 2012, to which priority is claimed pursuant to 35 U.S.C. §119(e) and which is hereby incorporated herein by reference in its entirety.

SUMMARY

Embodiments of the disclosure are directed to approaches for characterizing near field transducers. Some embodiments are directed to a system that includes an excitation light source configured to provide excitation radiation to a near field transducer (NFT) subassembly including an NFT optical antenna. The system comprises an optical filter configured to substantially pass a portion of photoluminescent radiation emitted by the NFT optical antenna in response to the excitation radiation and to substantially block the excitation radiation. A detector is configured to detect the portion of photoluminescent radiation and to output an output signal in response to detection of the portion of photoluminescent radiation.

Some embodiments are directed to a method for characterizing NFT subassemblies. Excitation radiation is provided to a near field transducer (NFT) subassembly. The output radiation from the NFT subassembly is filtered. Filtering the output radiation comprises passing a portion of photoluminescent radiation emitted by the NFT subassembly in response to the excitation radiation and substantially blocking the excitation radiation transmitted by the NFT subassembly. The portion of photoluminescent radiation is detected and an output signal is generated in response to the detecting.

These and other features and aspects of various embodiments may be understood in view of the following detailed discussion and accompanying drawings.

DETAILED DESCRIPTION

Figure 1:
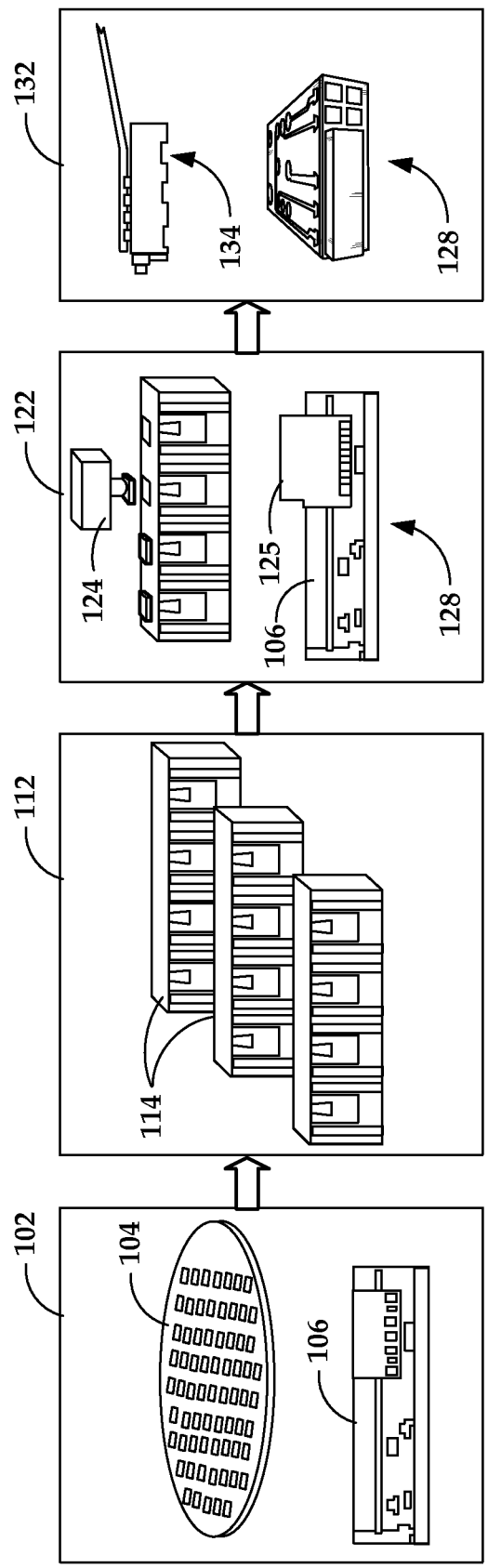
FIG. 1 shows a process flow diagram that illustrates a high-level summary of a portion of a process for fabricating a slider that may include an near field transducer (NFT) characterization step according to the approaches discussed herein.

The present disclosure relates to characterization of optical components used in applications such as heat assisted magnetic recording (HAMR). A HAMR device utilizes a magnetic recording media (e.g., hard disk) that is able to overcome superparamagnetic effects that limit the areal data density of typical magnetic media. In order to record on this media, a small portion of the media is locally heated while being written to by a magnetic write head. A coherent light source such as a laser can provide the energy to create these hot spots, and optical components, e.g., built in to a slider that houses the write head, are configured direct this energy onto the media.

When applying light to a HAMR medium, light from the light source is concentrated into a small hotspot over the track where writing is taking place. As a result of what is known as the diffraction limit, optical components cannot be used to focus light to a dimension that is less than about half the wavelength of the light. For example, the lasers used in some HAMR designs produce light with wavelengths on the order of 800-900 nm, yet the desired hot spot is on the order of 50 nm or less. Thus the desired hot spot size is well below half the wavelength of the light, and, due to diffraction, optical focusers cannot be used to obtain the desired hot spot size. As a result, an optical near field transducer (NFT) is employed to create these small hotspots on the media.

The NFT is a near-field optics device designed to reach local surface plasmon conditions at a designed wavelength. Example NFT transducers may include a plasmonic optical antenna or a metallic aperture and a focusing element. The focusing element concentrates light on the transducer region (e.g., at the focal region) near where the optical antenna or a metallic aperture is located. Example focusing elements may include solid immersion lenses (SIL), solid immersion mirrors (SIM), and/or three-dimensional channel waveguide for light delivery to a NFT. The NFT is designed to achieve surface plasmon resonance in response to this concentration of light.

Surface plasmons (SPs) are collective oscillations of surface charges that are confined to an interface between a dielectric and a metal. When SPs are resonantly excited by an external optical field, the field amplitude in the vicinity of the surface may be orders of magnitude greater than that of the incident field. Moreover, the region of enhanced field may be tightly confined to a spot much smaller than the incident wavelength. At resonance, a high electric field surrounds the NFT due to the collective oscillations of electrons at the metal surface. Part of this field will tunnel into a storage medium and get absorbed, thereby raising the temperature of a spot on the media as it being recorded.

The NFT may be located near an air bearing surface (ABS) of a slider used for magnetic data storage, and may be placed in close proximity to a write head that is also part of the slider.

This co-location of the NFT with the write head facilitates heating the hot spot during write operations. The focusing element, e.g., waveguide, and NFT may be formed as an integral part of the slider that houses the write head. Other optical elements, such as couplers, mirrors, prisms, etc., may also be formed integral to the slider. The optical elements used in HAMR recording heads are generally referred to as integrated optics devices.

The field of integrated optics relates to the construction of optics devices on substrates, sometimes in combination with electronic components, to produce functional systems or subsystems. For example, an integrated optics device may be built up on a substrate using layer deposition techniques. In reference now to FIG. 1, a process flow diagram illustrates a high-level, short summary of a portion of a process for fabricating a slider that includes integrated optics including an NFT and various optical coupling and/or light positioning elements. Block 102 represents a wafer-level stage. A wafer 104 is formed using semiconductor manufacturing processes (e.g., thin film deposition, chemical-mechanical polishing/planarization, etc.) and each wafer 104 generally includes a plurality of sliders (e.g., slider 106) that are later cut into bars for further processing. Each slider 106 includes an NFT subassembly comprising a waveguide focusing element and an NFT.

Block 112 represents an upstream stage where the wafer 104 has been cut into bars 114. Each bar 114 includes a plurality of sliders that are batch-processed. Stage 112 may involve attaching top bond pads (e.g., part of a slider-gimbal electrical interface). At the bar stage shown in Block 112, it can facilitate the manufacturing process to characterize the NFT subassemblies in the sliders 106 prior to proceeding with attachment of the lasers and subsequent manufacturing processing steps to complete the slider fabrication.

Block 122 represents a bar-level laser attach stage. Stage 122 may involve removing sacrificial cavity fill material, attaching the lasers and/or aligning the lasers with the NFT subassemblies. The lasers (e.g. laser diode 125) may be placed on the bars using a pick-and-place machine 124, and thereafter bonded to the slider (e.g., slider 106) via a reflow operation (e.g., application of heat to melt the solder bumps) to form assembly 128. Block 132 represents a stage for forming a head-gimbal assembly (HGA). Additional optical, electrical and/or magnetic tests may be performed on the completed head-gimbal assembly 134. In some cases, the manufacturing process may be facilitated by testing the NFT subassemblies at the bar stage before proceeding with the laser attachment and subsequent manufacturing steps.

Figure 2:
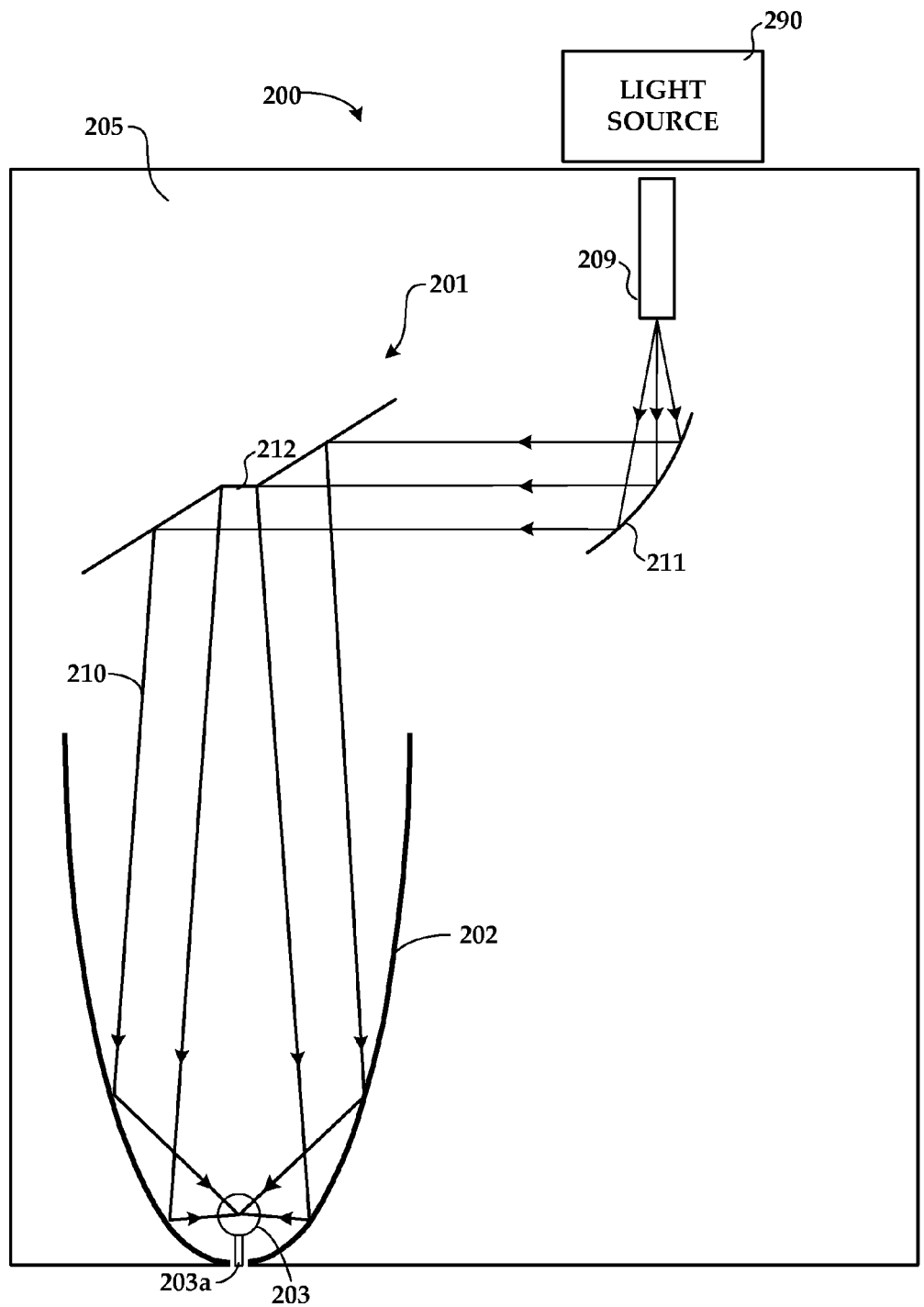
FIG. 2 provides a cross-sectional diagram that illustrates an NFT subassembly that can be characterized using the approaches discussed herein.
Figure 3:
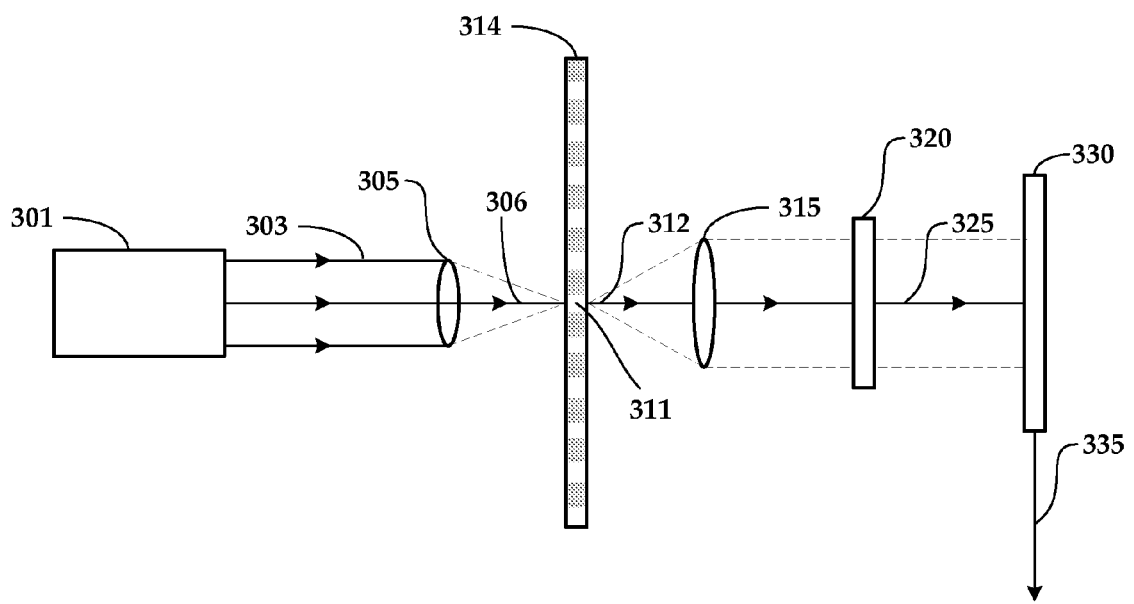
FIG. 3 depicts a system for characterizing NFT subassemblies in accordance with some embodiments.

FIG. 2 provides a cross-sectional diagram that illustrates an NFT subassembly 200 that can be characterized using the approaches discussed herein. The NFT subassembly 200 shown in FIG. 2 is fabricated in a slider 205 and includes input waveguide coupler 209, first mirror 211, second mirror 212, solid immersion mirror 202, and NFT optical antenna 203. NFT subassemblies 200 that operate by end-fire technique as shown in FIG. 2 may in incorporated into each slider 106 of a bar 114 shown in FIG. 1. The NFT subassembly 200 illustrates one particular configuration, although it will be appreciated that many configurations of NFT subassemblies are possible and can be characterized by the approaches discussed herein.

In the example illustrated in FIG. 2, the NFT subassembly 200 receives light emitted from a light source 290 via an input waveguide coupler 209 which is a three-dimensional channel waveguide of finite wide waveguide core. In normal use, the light source 290 may comprise an edge emitting or surface emitting laser diode, for example. The light emerging from the waveguide coupler 209 is directed in a solid immersion mirror (SIM), or planar solid immersion mirror (PSIM) indicated by way of SIM sidewall 202 in FIG. 2, by a first mirror 211 and a second mirror 212. An optical antenna NFT 203 is located at the focus point of the SIM 202.

The optical antenna NFT 203 shown in FIG. 2 comprises a "lollipop" configuration that combines a circular disc with a peg, although other configurations may be used. The lollipop dimensions are selected to function as an antenna for the incident light, to resonate at the excitation wavelength, and to transfer energy into the peg and thus to the medium via the feedgap at the tip 203a of the NFT optical antenna 203. The NFT optical antenna 203 (also referred to as an NFT) is a transducer that can be made of any known plasmonic material (e.g., Au, Ag, Cu, ZrN) and may be positioned at or near the focal region of the light 210.

The waveguide core 201 may be formed from any material that has a higher index of refraction than cladding. For example, the waveguide core 201 may be made from $Ta_2O_5$, $TiO_2$, ZnS, SiN. The PSIM 202 may be formed as a parabolic cutout of surrounding dielectric waveguide material (e.g., $Al_2O_3$, $SiO_2$, SiOxNy, MgO, $HfO_2$, $Y_2O_3$, $Ta_2O_5$, TiOx). The cutout may be formed from/coated with a reflective material (e.g., Au, Al), so that light rays 210 entering the PSIM 202 by way of waveguide core 201 are focused to a focal region to strongly couple to the NFT optical antenna 203 and generate surface plasmons.

As previously discussed in connection with FIG. 1, the manufacturing process can be facilitated by characterization of the optical components of a slider, including the NFT subassembly, such as NFT subassembly 200. For example, NFT subassemblies can be tested at the wafer stage, the bar stage, or even individually prior to laser placement.

Dark field microscopy has been attempted to characterize optical antennas by measuring the light scattering from NFT, however this characterization technique is not suitable for in the presence of an incident beam ("bright field") in actual devices. Characterization of the NFT by the thermo-reflectance pump/probe method measures optical changes due to absorption of the NFT, however, the pump/probe method can suffer from variation due to thermal environment. Some characterization methods are be insensitive to certain parameters that are useful to track in a manufacturing environment.

According to embodiments discussed herein, characterization of the NFT subassemblies may be accomplished by sensing filtered photoluminescent radiation emitted by the NFT in response to high energy excitation radiation. The photoluminescent radiation is strongly enhanced by the local surface plasmons that are generated at the NFT surface. The photoluminescent radiation generated in the NFT includes wavelengths shorter than the excitation radiation by two-photon excitation. Two-photon luminescence is luminescence excited by two-photon absorption. Two-photon induced photoluminescence in noble metals such as gold and silver is generally considered as a three-step process. Electrons from occupied d bands are first excited by two-photon absorption to unoccupied states of the sp-conduction band. Second, subsequent intraband scattering processes move the electrons closer to the Fermi level. Third, the relaxation of the electron-hole pair recombines either through nonradiative processes or by emission of luminescence. The emission of luminescence is proportional to $E^4$, where E denotes the electric-field amplitude. Local surface plasmons at the surface of the NFT antenna enhance the luminescence significantly.

In various configurations, the characterization system includes shortwave pass spectral filters, notch filters and/or beam splitters with a wavelength edge that are used to separate the bright field light (e.g., the excitation light) from the photoluminescent light emanating from the NFT.

Figure 4A:
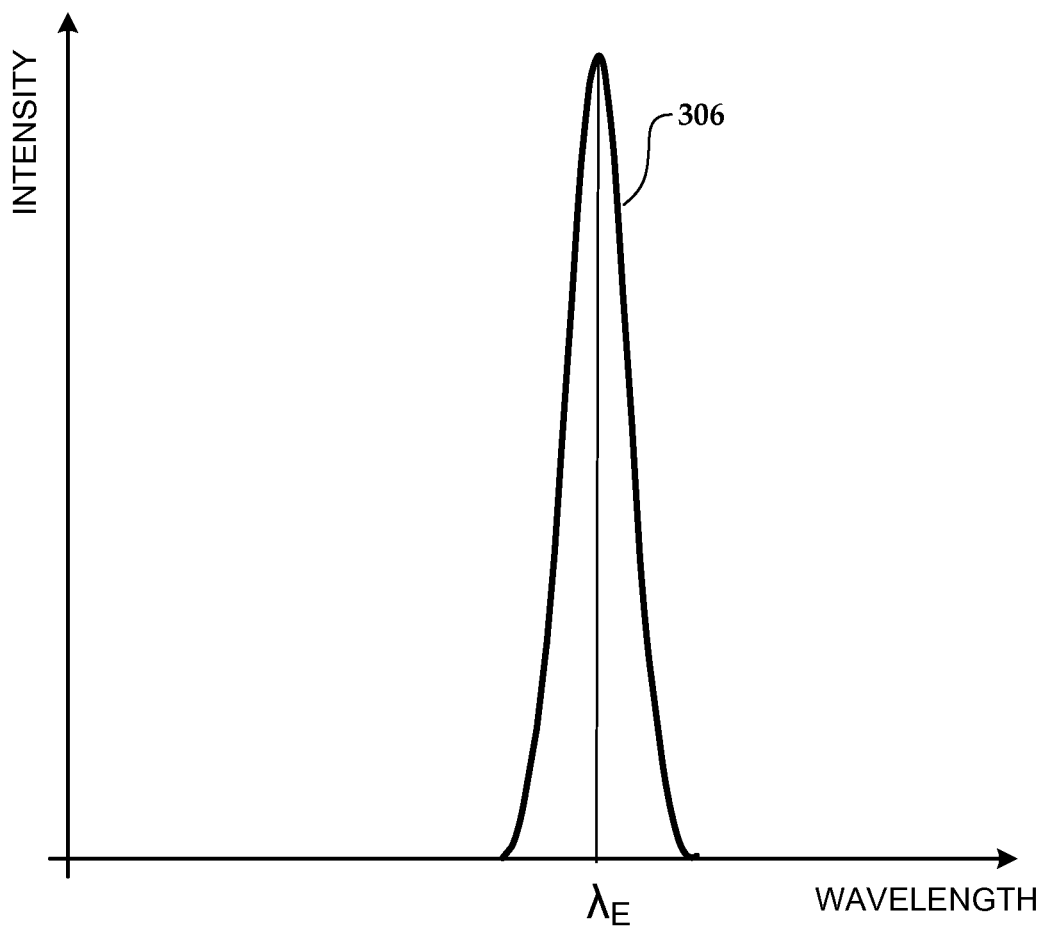
FIG. 4A provides an example spectral characteristic of the excitation radiation for the systems of FIGS. 3 and 5.
Figure 4B:
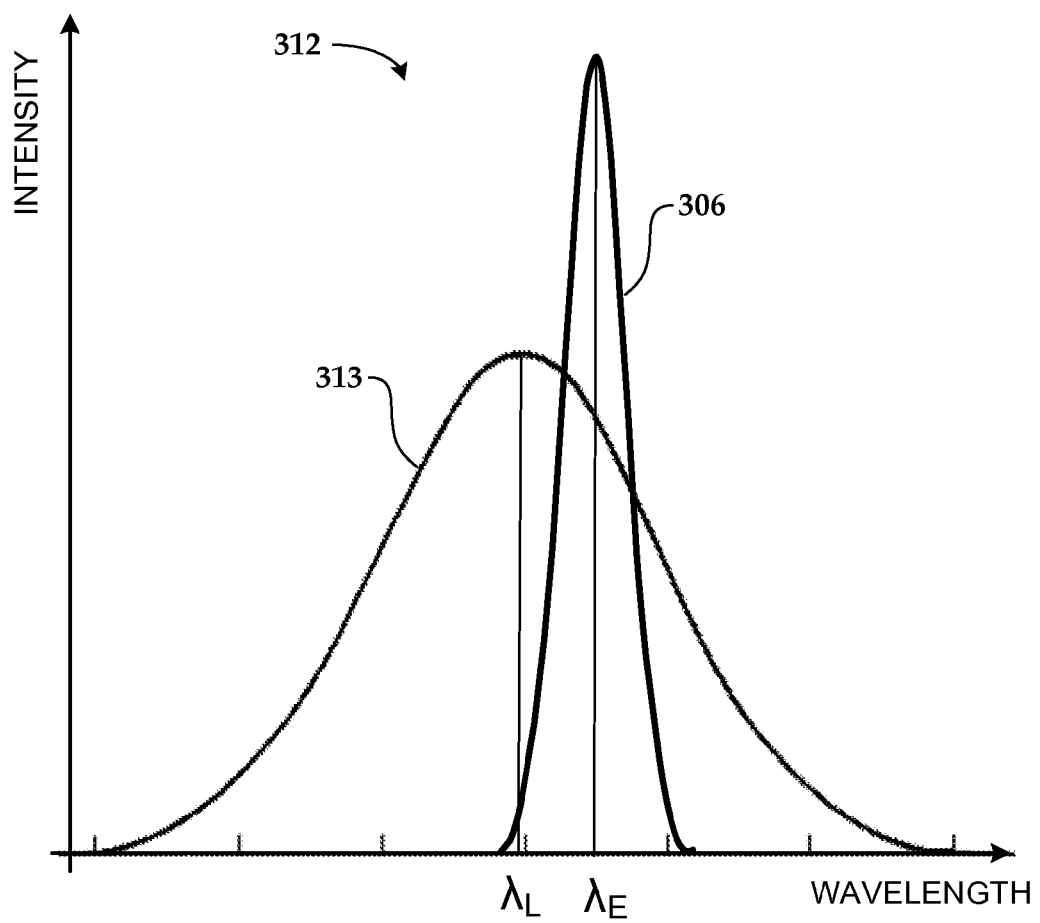
FIG. 4B provides an example spectral characteristic of photoluminescent radiation emitted by an NFT in response to the excitation radiation.
Figure 4C:
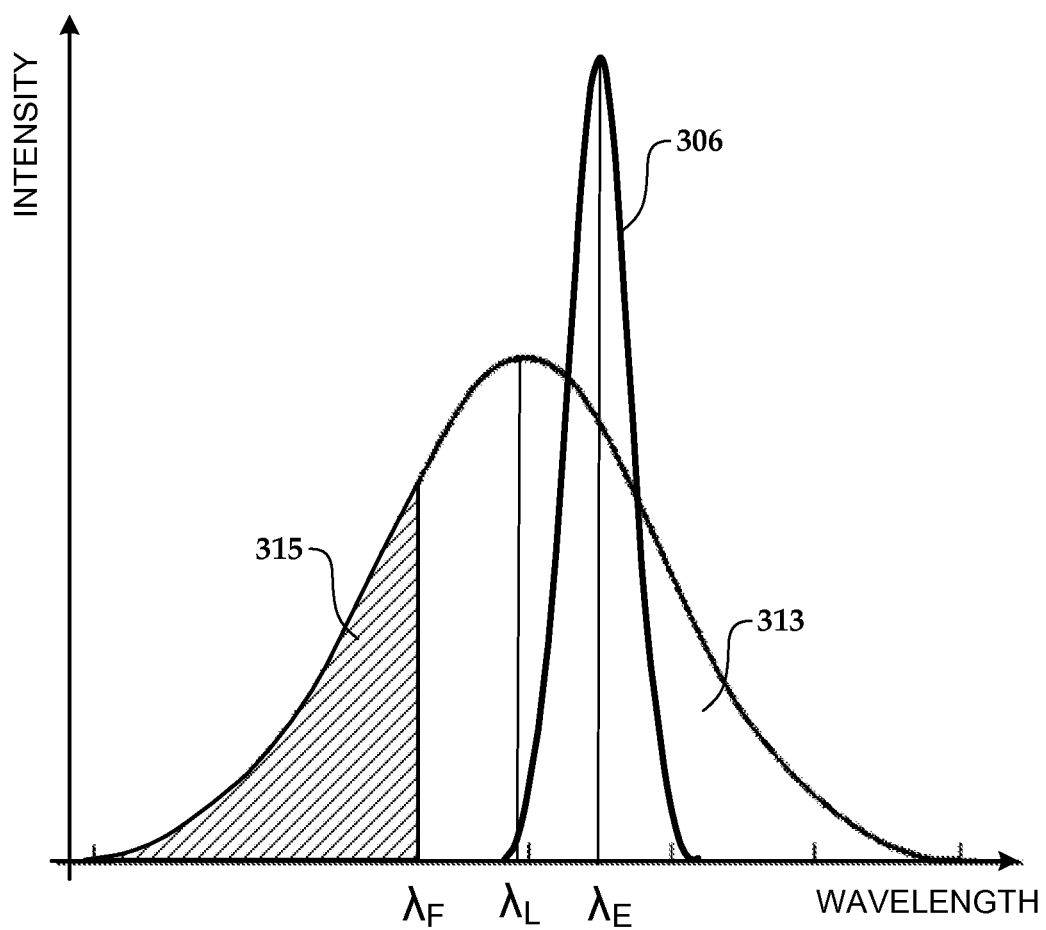
FIG. 4C illustrates shortwave pass filtered radiation that is used to characterize the NFT under test in accordance with various embodiments.

A system for characterizing NFT subassemblies in accordance with some embodiments is described with reference to FIGS. 3 and 4A-4C. A laser 301 emits excitation radiation 303 that passes through a focusing lens 305 and illuminates one of the NFT subassemblies 311 disposed on bar 314. FIG. 4 provides an exemplary spectral distribution of the focused excitation radiation 306 that is centered at wavelength $\lambda_E$. The spectral distribution diagrams of FIGS. 4A-C are idealized as Gaussian distributions of arbitrary peak magnitudes, however, it will be appreciated that, in general, the distributions need not be Gaussian. In response to the excitation radiation 306, the NFT subassembly 311 emits white-light super-continuum photoluminescence 313 at the feedgap and tip of the optical antenna (see, 203a, FIG. 2). The NFT subassembly also transmits the portion of the excitation radiation that is not absorbed in the NFT subassembly 311.

An exemplary spectral distribution of the electromagnetic radiation 312 emerging from the NFT subassembly 311 that includes both a photoluminescent radiation component 313 and an excitation radiation component 306, is shown in FIG. 4B. In this example, the photoluminescent radiation component 313 is shown as having an arbitrary peak or central wavelength, $\lambda_L$, and the excitation radiation component 306 is shown as having an arbitrary peak or central wavelength, $\lambda_E$. Although the spectral distributions and magnitudes of FIGS. 4A-4C do not necessarily correspond to actual spectral distributions and magnitudes of the photoluminescent and excitation radiation, FIG. 4C illustrates that the photoluminescent radiation 313 emitted by the NFT includes shorter wavelength radiation and/or has shorter peak or central wavelength when compared to the excitation radiation 306.

The radiation 312 that emerges from the NFT 311 is collected and collimated by a lens 315 and passes through a shortwave pass filter 320 having a cutoff wavelength, $\lambda_F$. The shortwave pass filter 320 substantially removes components of the radiation 312 having a wavelength longer than $\lambda_F$. As such, the shortwave pass filter 320 substantially absorbs or blocks the excitation radiation component 306 and also absorbs or blocks that portion of the photoluminescent radiation that has wavelength greater than $\lambda_F$. The shortwave pass filter substantially passes wavelengths of the photoluminescent radiation with wavelengths greater than $\lambda_F$, including radiation 325 shown in FIG. 4C.

Returning now to FIG. 3, the filtered radiation 325 impinges on a detector 330, such as a photomultiplier tube (PMT). The PMT provides an electrical signal output 335 in response to the incident filtered radiation 325 that can be used to measure the filtered photoluminescent radiation emitted by the NFT subassembly.

Figure 5:
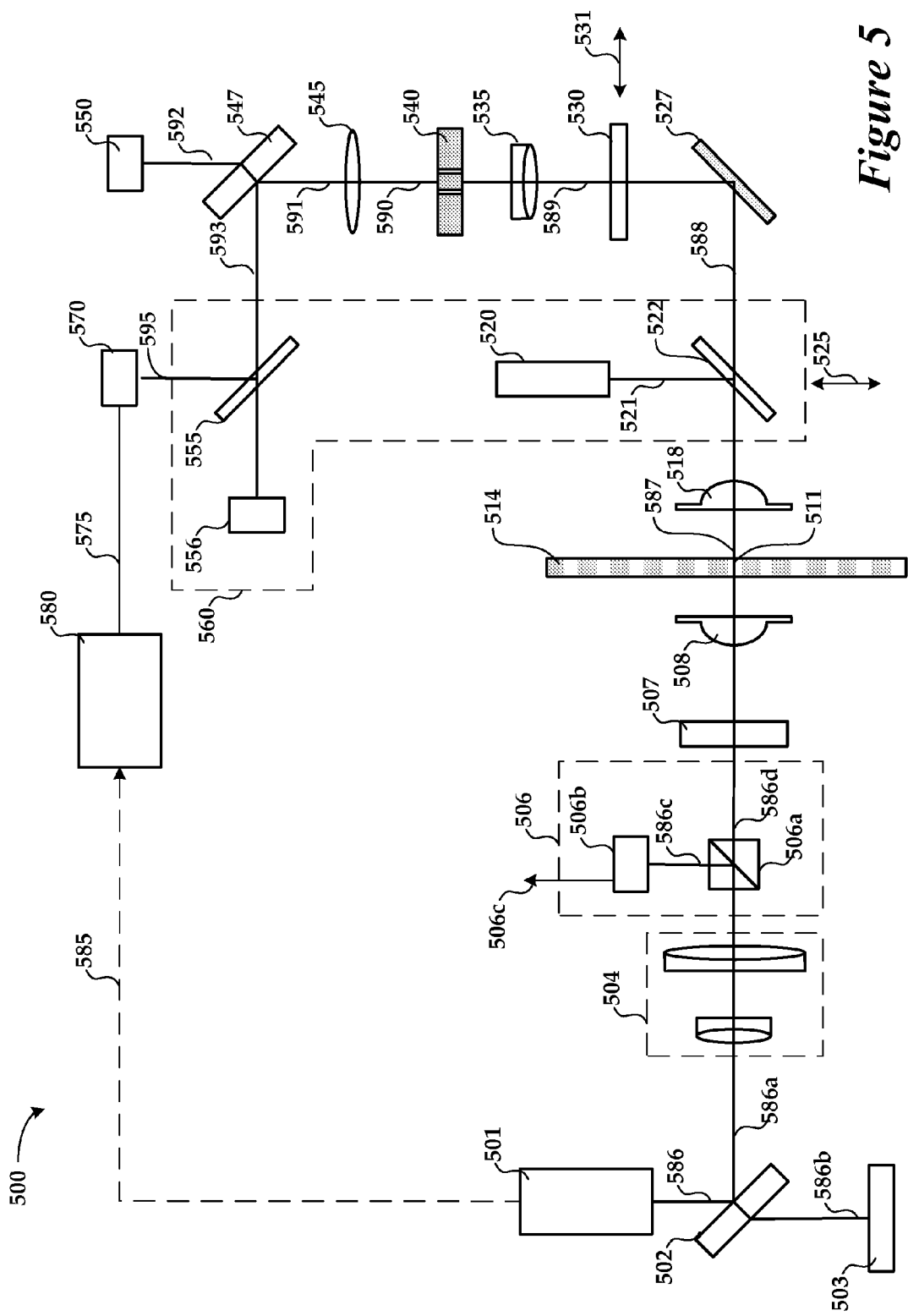
FIG. 5 is a block diagram of a system for characterizing NFT subassemblies according to various embodiments.

FIG. 5 shows another embodiment of a system 500 for characterizing the NFTs by detecting photoluminescent light emanating from the NFTs in response to excitation radiation. For example, in some particular embodiments, the high energy excitation radiation is provided by a mode locked femto second or pico second laser 501, e.g., a Ti:sapphire laser emitting 160 femto second pulses at a repetition rate of 76 MHz and having a wavelength of about 825 nm±30 nm. In some cases, it may be desirable to reduce the intensity of the excitation light 586 that is incident on the NFT subassembly under test. In these cases a beam sampler may be used to pass a portion of the excitation light to a beam dump. As shown in FIG. 5, the excitation light 586 emitted by the laser 501 reflects from an optional Fresnel beam sampler 502. A portion 586b of the excitation radiation is transmitted through the Fresnel sampler 502 to a beam dump 503. Another portion 586a of the excitation radiation is directed toward an optional beam expander 504 that expands the beam of the excitation radiation 586a emitted by the laser. In some cases, the system 500 optionally includes a subsystem 506 configured to monitor the excitation radiation 586a at the output of the beam expander 504. The optional excitation radiation monitor 506, can include, for example, a neutral, non-polarizing beam splitter cube 506a that splits off a sample 586c of the excitation radiation 586a and directs the sample radiation 586c to a photodetector 506b. The photodetector 506b generates a signal 506c in response to the incident sample radiation 586c.

The excitation radiation 586d passes through an achromatic half wavelength wave plate 507 that rotates the polarization direction of radiation 586d to the desired direction for NFT excitation. The excitation radiation 586d is focused by focusing lens 508 onto the input waveguide coupler (or grating coupler) in subassembly 511 being tested by end-fire technique. For example, a suitable lens for lens 508 is an aspherical lens that has a numerical aperture (NA) of about 0.25. In some test setups, the NFT subassembly 511 being tested is disposed on a bar 514 that includes many NFT subassemblies. In response to the excitation radiation 586d, the NFT subassembly 511 being tested emits photoluminescent radiation and also a portion of the excitation radiation is transmitted through the NFT subassembly 511. Thus, the radiation 587 emanating from the NFT subassembly 511 is a combination of the photoluminescent radiation and the excitation radiation, as previously discussed.

The combined radiation 587 output from the NFT subassembly 511 under test is collimated and collected by a lens 518 of high numerical aperture, e.g., NA of about 0.90. To image the radiation exiting surface of the NFT subassembly 511, the system 500 may include an imaging subsystem 560. The imaging subsystem includes a fiber bundle white light source 520 that provides white light 521 for imaging the NFT subassembly 511. The white light 521 is coupled into the light beam 588 by a broadband mirror 522. Arrow 525 indicates that components of the imaging subsystem, e.g., the white light source 521 and mirror 522 may be used for set up and then removed from the beam path. Radiation 588 includes excitation radiation transmitted through the NFT subassembly 511, includes photoluminescent radiation emitted by the NFT subassembly in response to the excitation radiation. In some configurations, the imaging system 560 is used to position the NFT subassembly 511. In these configurations, the white light 521 generated by the white light source 520 will not be a component of radiation 588 when the photoluminescence of the NFT subassembly 511 is being measured.

Figure 6:
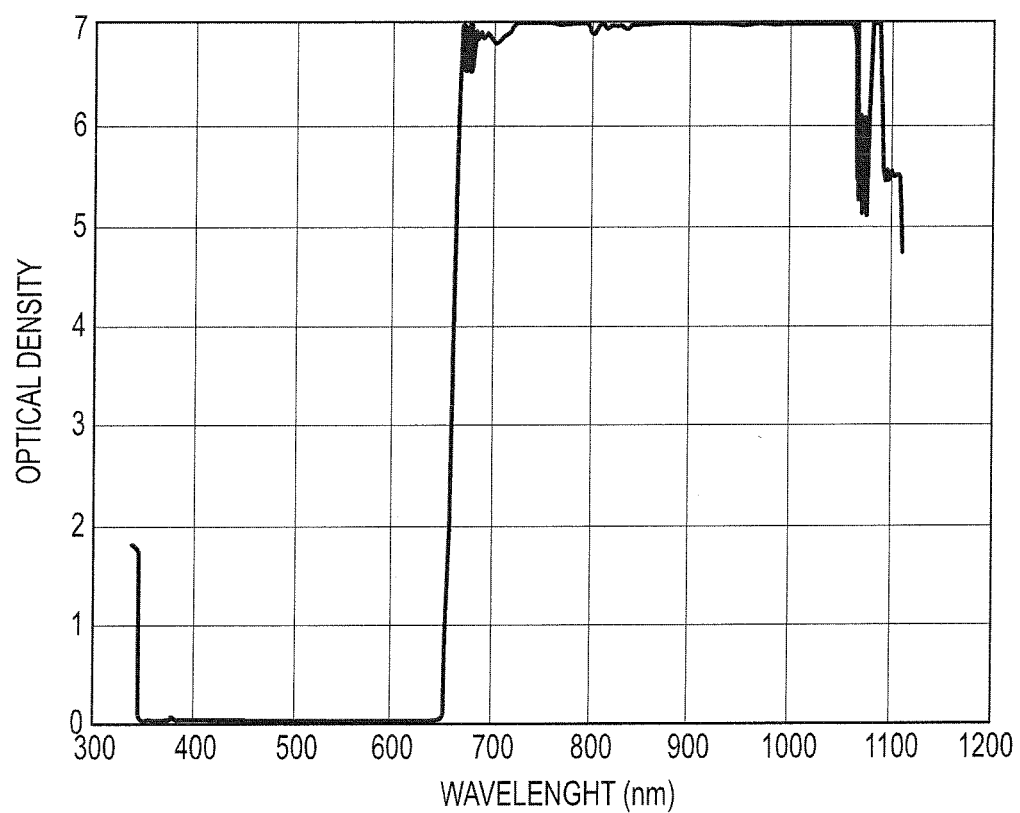
FIG. 6 shows a possible spectral characteristic for the shortwave pass filter used in the system of FIG. 5.

Radiation 588 is optionally redirected through mirror 527 and through a shortwave pass spectral filter 530. The shortwave pass filter 530 substantially blocks (absorbs) the excitation radiation and substantially passes a portion of the photoluminescent radiation emitted by the NFT. FIG. 6 shows a possible spectral characteristic for the filter 530. A filter having the characteristics of FIG. 6 has an optical density of $10^{-7}$ and blocks transmission by a factor of about $10^{-7}$ in the wavelength range longer than the cut-off wavelength (which is 650 nm in FIG. 7), where the excitation radiation (e.g., 825 nm+30 nm) is located. In contrast, the filter shown in FIG. 6 substantially passes radiation (has an optical density close to 0 or 100% transmission) in the wavelength range from about 320 nm to about 650 nm. Arrow 531 indicates that the filter 530 may be moved out of the radiation path during measurement of the transmitted excitation radiation.

Figure 7:
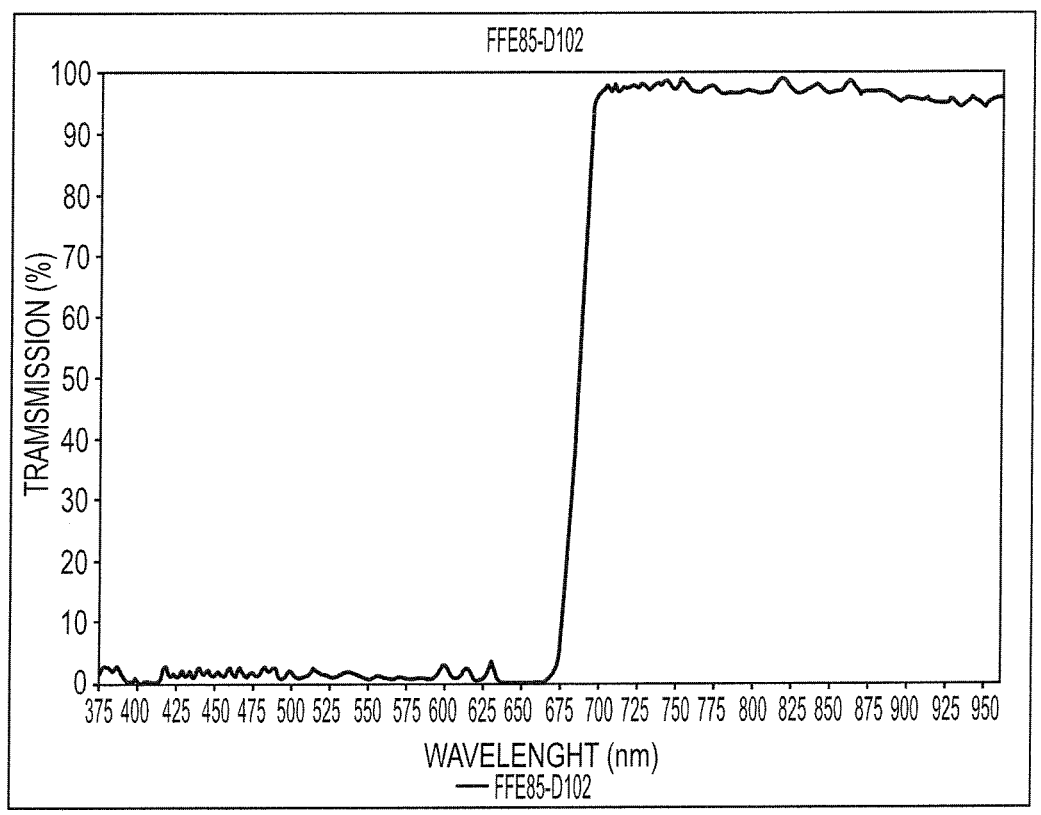
FIG. 7 shows a possible spectral characteristic of a suitable dichroic beam splitter used in the system of FIG. 5.

After the filter 530, a confocal detection scheme is used. Radiation 589 that passes through the filter 530 subsequently passes through a non-coated or broad-band coated planoconvex imaging lens 535 or a doublet. An iris diaphragm or a slit 540 is placed near the focal point of the imaging lens 535 to reduce the background noise. Radiation 590 that passes through the iris diaphragm or slit 540 is imaged by a biconvex lens 545 and through a dichroic beam splitter 547. The dichroic beam splitter 547 has a 685 nm edge that separates the incoming radiation 591 into two spectrally distinct beams. Any radiation with wavelength above the 685 nm edge is transmitted, whereas radiation with wavelength below the 685 nm edge is reflected. The spectral characteristic of a suitable dichroic beam splitter is shown in FIG. 7. The incoming radiation 591 is separated by the dichroic beam splitter 547 into a first radiation beam 592 with wavelength greater than 685 nm and a second radiation beam 593 with wavelength less than 685 nm. The shortwave pass filter 530 in combination with the dichroic beam splitter 547 reject the excitation radiation wavelengths from the second radiation beam 593 by a factor of about $10^{-7}$, or about $10^{-10}$ or even about $10^{-14}$.

The first radiation beam 592 is directed to a photodetector 550 configured to measure the excitation radiation transmitted through an NFT subassembly. The second radiation beam 593 comprises the components from the photoluminescence from the NFT under test 511 and the light from the white light source 520 that was reflected by the NFT bar 514. Optical element 555 directs the photoluminescent radiation to both or either of PMT 570 and CCD 556. Optical element 555 is on a translation stage and may be a beam splitter or moveable mirror. If optical element 555 is a moveable mirror, the moveable mirror directs the luminescence to PMT 570 or to CCD 556. If optical element 555 is a beam splitter, optical element directs the luminescence to both the PMT 570 and the CCD 556. With the white-light moved in the light path and without the presence of shortwave pass filter 530 in the light path, the light transmitted through a device, including the NFT radiation, and the white light 594 reflected from a device is imaged onto a cooled charge coupled device (CCD) that is a part of the imaging subsystem 560; with the white-light moved out of the light path and the shortwave pass filter 530 moved into the light path, the two-photon induced photoluminence from NFT is either directed to PMT 570 or CCD 556 if 555 is a mirror, or, is split into both PMT 570 and CCD 556 if 555 is a beam splitter. The photoluminescence image of the NFT bar 514 can be viewed using the CCD without the presence of white light radiation and with the presence of shortwave pass filter. The white-light source is removed from the optical path to measure photoluminescence (imaging and detection).

The photoluminescence 595 is detected by photomultiplier tube (PMT) 570. In response to the photoluminescence 595, the PMT 570 generates an electrical signal 575 that is based on the amount of radiation incident on the PMT 570. The electrical signal 575 is amplified using a lock-amplifier that is locked to the repetition frequency of the laser pulses.

Figure 8:
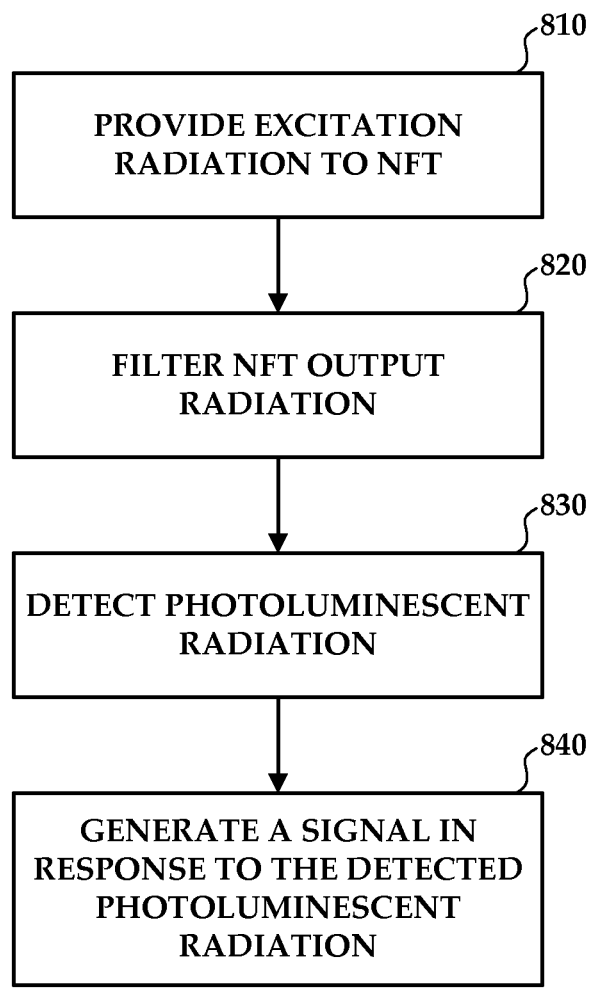
FIG. 8 is a flow diagram of a method to characterize an NFT subassembly in accordance with some embodiments.

Some embodiments are directed to methods for characterizing NFT subassemblies. With reference now to FIG. 8, a method to characterize an NFT subassembly includes providing 810 excitation to the NFT subassembly. The excitation radiation generates photoluminescence in the NFT at a shorter wavelength than the excitation radiation. The radiation output from the NFT includes both the excitation radiation and the photoluminescent radiation. The excitation radiation is substantially separated 820 from the photoluminescent radiation, e.g., using a shortwave pass filter and/or dichroic beam splitter. The photoluminescent radiation is detected 830 by a detector that generates 840 a signal indicative of the amount of photoluminescent radiation. The amount of photoluminescent radiation is related to the functionality of the NFT and the generated signal can be used to determine how well a particular NFT subassembly is working and/or to compare the relative quality of NFT subassemblies on a bar.

Figure 9A:
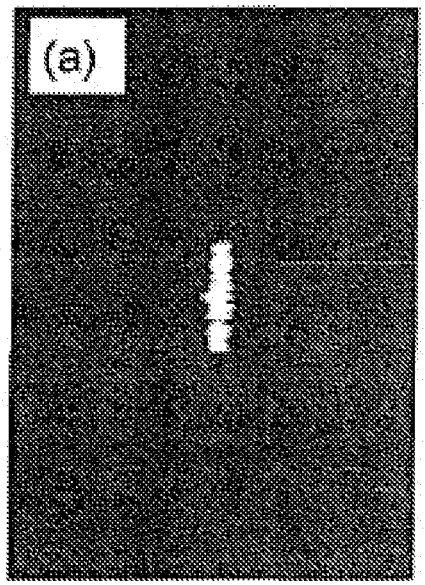
FIGS. 9A-9D show optical images of the transmitted light from a gap-plasmon NFT acquired using the system shown in FIG. 5.
Figure 9B:
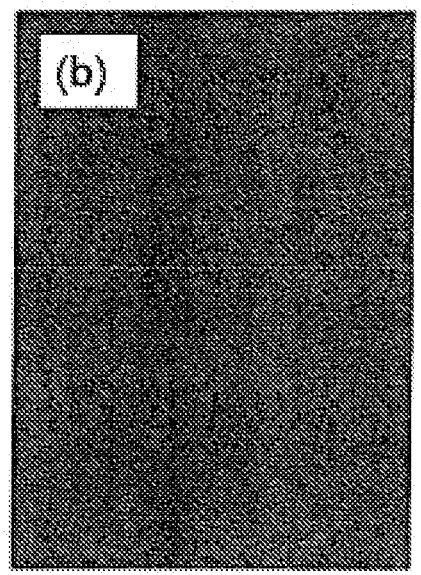
Figure 9C:
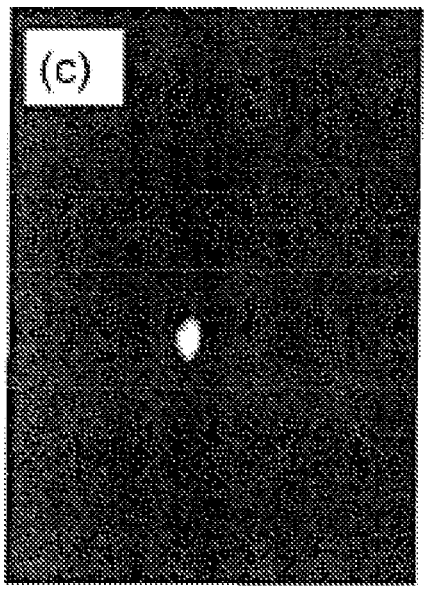
Figure 9D:
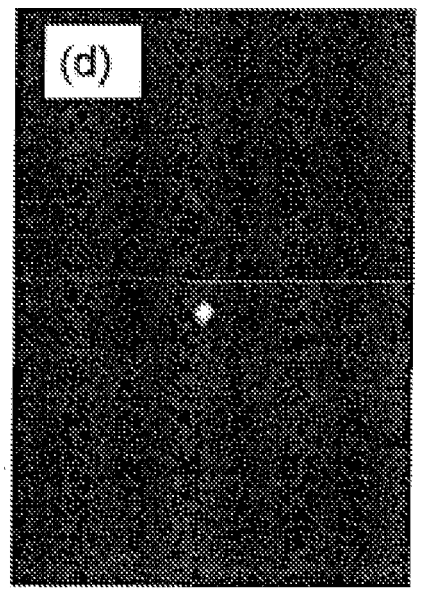

FIGS. 9A, 9C and 9D show optical images of the transmitted light from a gap-plasmon NFT acquired using the system shown in FIG. 5. In FIG. 9A, the CCD shows the transmission image dominated by the excitation radiation. In FIG. 9A, the shortwave pass filter is not inserted in the light path so that all the light, including the transmitted light and radiation emanating from the NFT, is observed (both photoluminescent radiation and the transmitted excitation radiation, which dominates). For the image of FIG. 9A, the CCD gain=1 and the exposure time is <1/500 second. For comparison, FIG. 9B shows the photoluminescent radiation for a device that does not have an NFT. As would be expected, the photoluminescent radiation for a device without an NFT is very weak and cannot be detected in FIG. 9B. In FIG. 9B, the shortwave pass filter is inserted in the beam. For the image of FIG. 9B, the CCD gain=4, the exposure time is 2 seconds, and the incident (average) power=3.6 mW). Incident power is the average power onto a device, i.e., the intensity of radiation 586d in FIG. 5.

FIGS. 9C and 9D show the photoluminescent radiation from devices with NFT. The shortwave pass filter is inserted in the light path and the white-light source is removed out of the light path. In each of FIGS. 9C and 9D, the photoluminescent radiation creates one bright optical spot. By comparing FIGS. 9C and 9D to FIG. 9B, it is apparent that the presence of the NFT greatly enhances the photoluminescent radiation emerging from the device under test. For FIGS. 9C and 9D, the CCD gain=4, the exposure time=2 seconds, and the incident (average) power is reduced to only 0.8 mW.

Figure 10:
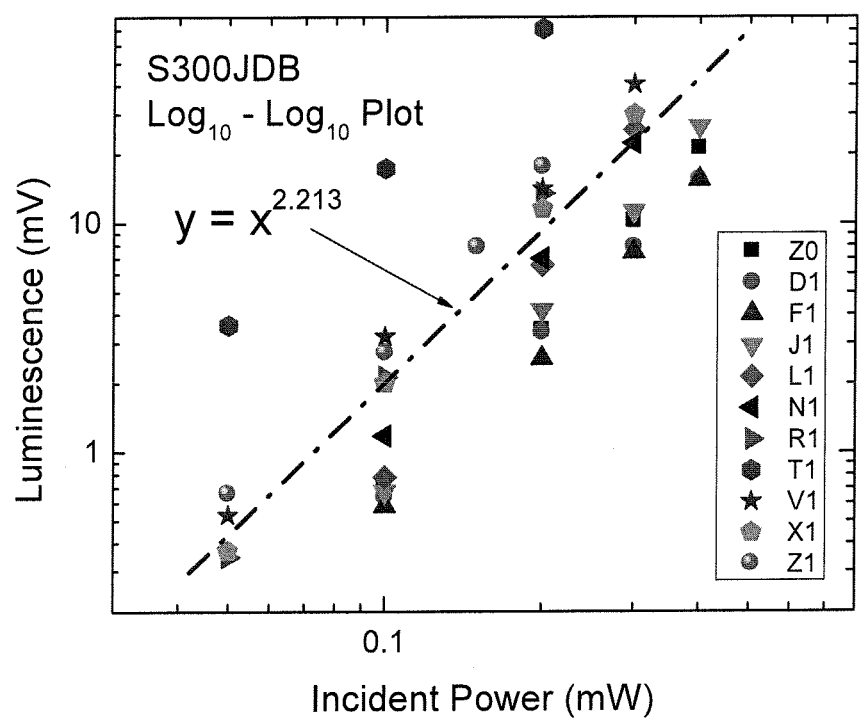
FIG. 10 shows a log-log plot of photoluminescence vs. monitor power, obtained using the NFT characterization system described in FIG. 5 for devices that have a lollipop NFT.

FIG. 10 shows a log-log plot of photoluminescence vs. monitor power, obtained using the NFT characterization system described in FIG. 5 for devices that have a lollipop NFT. The fit of luminescence with incident power of 2.2 is observed, which is a signature of two-photon luminescence.

Figure 11:
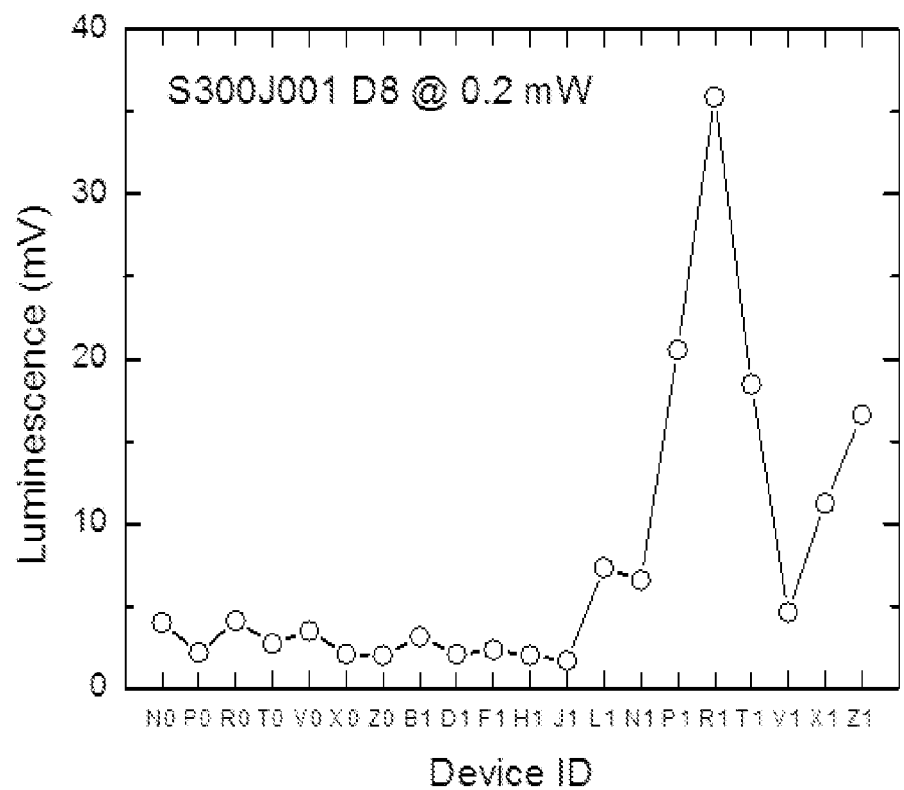
FIG. 11 shows the variation in luminescence with for lollipop NFTs measured using the NFT characterization system shown in FIG. 5.

FIG. 11 shows the variation in photoluminescence for lollipop NFTs measured using the NFT characterization system shown in FIG. 5. A bar of 64 NFT subassemblies with lollipop NFTs was tested using the characterization approaches discussed herein. In this example, the photoluminescence varied across the bar.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A system comprising:
    a near field transducer (NFT) subassembly including an input coupler proximate a first surface and an NFT optical antenna proximate a second surface;
    an excitation light source configured to provide excitation radiation to the near field transducer subassembly;
    an optical filter configured to substantially pass a portion of photoluminescent radiation emitted by the NFT optical antenna in response to the excitation radiation and to substantially block the excitation radiation;
    a detector configured to detect the portion of photoluminescent radiation and to output an output signal in response to detection of the portion of photoluminescent radiation;

a focusing lens configured to focus the excitation radiation onto the input coupler of the NFT subassembly; and an objective lens configured to collect photoluminescent radiation emitted by the NFT toward the optical filter.

2. The system of claim 1, wherein the excitation radiation comprises femto-second or pico second laser pulses.

3. The system of claim 1, wherein the optical filter is configured to substantially pass radiation having wavelengths shorter than the excitation light.

4. The system of claim 1, further comprising an imaging subsystem configured to provide a visual image of the NFT.

5. The system of claim 4, wherein the imaging subsystem comprises:
a white light source; and
a charge coupled device (CCD).

6. The system of claim 1, wherein the detector comprises a photomultiplier tube (PMT).

7. The system of claim 1, further comprising an amplifier coupled to receive the output signal, wherein the amplifier is locked-in to a repetition frequency of the excitation radiation.

8. A system comprising:
an excitation light source configured to provide excitation radiation to a near field transducer (NFT) subassembly including an NFT optical antenna;
an optical filter configured to substantially pass a portion of photoluminescent radiation emitted by the NFT optical antenna in response to the excitation radiation and to substantially block the excitation radiation;
a detector configured to detect the portion of photoluminescent radiation and to output an output signal in response to detection of the portion of photoluminescent radiation; and
a monitoring subsystem configured to monitor the excitation radiation.

9. The system of claim 8, wherein the monitoring subsystem comprises:
an input side photodetector configured to generate a signal in response to the excitation radiation incident on the input side photodetector;
a beam splitter disposed in between the laser and the NFT subassembly, the beam splitter configured to split the excitation radiation so that a first portion of the excitation radiation travels along a first input path toward the input side photodetector and a second portion of the excitation radiation travels along a second input path toward the NFT subassembly.

10. The system of claim 8, wherein the monitoring subsystem comprises an output side photodetector configured to generate a signal in response to output radiation transmitted through the NFT subassembly, the output radiation dominated by the excitation radiation.

11. The system of claim 10, further comprising a beam splitter disposed between the NFT and the output side photodetector, the beam splitter configured to split the output radiation so that a first portion of the output radiation having wavelengths longer than an edge wavelength of the beam splitter travels along a first output path toward the output side photodetector and a second portion of the output radiation having wavelengths shorter than the edge wavelength travels along a second output path toward the detector.

12. A method, comprising:
providing excitation radiation to a near field transducer (NFT) subassembly;
filtering output radiation from the NFT subassembly, the filtering comprising passing a portion of photoluminescent radiation emitted by the NFT subassembly in response to the excitation radiation and substantially blocking the excitation radiation transmitted by the NFT subassembly; and
detecting the portion of photoluminescent radiation and generating an output signal in response to the detecting, wherein filtering the output radiation comprises filtering using one or more of a shortwave pass optical filter and a dichroic beam splitter.

13. The method of claim 12, wherein filtering the output radiation comprises filtering using a shortwave pass optical filter.

14. The method of claim 12, wherein filtering the output radiation comprises filtering using a dichroic beam splitter.

15. The method of claim 12, wherein detecting the portion of photoluminescent radiation comprises detecting using a photomultiplier tube.

16. The method of claim 12, wherein providing excitation radiation to an NFT subassembly comprises providing laser pulses at a repetition rate.

17. The method of claim 12, wherein filtering the output radiation from the NFT subassembly comprises substantially blocking the excitation radiation and substantially passing the portion of the photoluminescent radiation.

18. The method of claim 17, wherein blocking the excitation radiation comprises blocking the excitation radiation by a factor of about $10^{-7}$.

19. A method, comprising:
providing excitation radiation to a near field transducer (NFT) subassembly;
filtering output radiation from the NFT subassembly, the filtering comprising passing a portion of photoluminescent radiation emitted by the NFT subassembly in response to the excitation radiation and substantially blocking the excitation radiation transmitted by the NFT subassembly;
detecting the portion of photoluminescent radiation and generating an output signal in response to the detecting; and
signal processing the output signal including amplifying the output signal using circuitry that locks into a repetition rate of the excitation radiation.

* * * * *